United States Patent [19]

Takahashi et al.

[11] Patent Number: 4,921,786
[45] Date of Patent: May 1, 1990

[54] NOVEL NAD SYNTHETASE, ASSAY METHOD USING SAID NOVEL NAD SYNTHETASE AND A PROCESS FOR PRODUCTION THEREOF

[75] Inventors: Mamoru Takahashi; Hideo Misaki; Shigeyuki Imamura; Kazuo Matsuura, all of Shizuoka, Japan

[73] Assignee: Toyo Jozo Kabushiki Kaisha, Shizuoka, Japan

[21] Appl. No.: 94,813

[22] Filed: Sep. 10, 1987

[30] Foreign Application Priority Data

Sep. 10, 1986 [JP] Japan .................................. 61-213679
Jul. 30, 1987 [JP] Japan .................................. 62-191018

[51] Int. Cl.$^5$ .............................................. C12Q 1/00
[52] U.S. Cl. ......................................... 435/4; 435/15; 435/16; 435/17; 435/21; 435/25; 435/26; 435/27; 435/28; 435/183
[58] Field of Search ...................... 435/183, 4, 15, 16, 435/21, 25, 26, 27, 28

[56] References Cited

U.S. PATENT DOCUMENTS

4,767,712  8/1988  Misaki et al. .

FOREIGN PATENT DOCUMENTS

2545504  11/1984  France .
59-314325  11/1984  Japan .

OTHER PUBLICATIONS

Lambrecht et al.–Chem. Abst. vol. 103 (1985), p. 213322p.
Misaki et al.–Chem. Abst. vol. 103 (1985), p. 19439s.
Richard L. Spencer et al.–*Journal of Biological Chemisty*, vol. 242, No. 3 (Feb. 1967) pp. 385–392, "Biosynthesis of Diphosphopyridine Nucleotide".
"Isolation of Different Thermophilic Enzymes from *Bacillus stearothermophilus*", *Experientia*, vol. 29, No. 8, Aug. 1973, By. H. Hengartner et al., pp. 941–942.
"Biosynthesis of Diphosphopyridine Nucleotide", *Journal of Biological Chemistry*, vol. 233, No. 2, 1958, by J. Preiss et al., pp. 493–500.
"Biosynthesis of Diphosphopyridine Nucleotide", *Journal of Biological Chemistry*, vol. 236, No. 2, 1960, By John Imsande et al., pp. 525–530.
"Purification and Properties of Yeast Nicotinamide Adenine Dinucleotide Synthetase", *Journal of Biological Chemistry*, vol. 247, No. 15, 1972, By Cheng Kai Yu et al., pp. 4794–4802.
"Pathway of Diphosphopyridine Nucleotide Biosynthesis in *Escherichia coli*", *Journal of Biological Chemistry*, vol. 236, No. 5, 1961, By John Imsande, pp. 1494–1497.

Primary Examiner—Sam Rosen
Attorney, Agent, or Firm—Young & Thompson

[57] ABSTRACT

A novel NAD synthetase is produced by culturing a broth of *Bacillus stearothermophilus* H-804 FERM BP-1408. This new enzyme selectively catalyzes the reaction ATP + deamide-NAD +

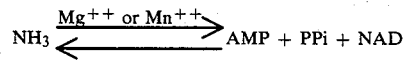

without catalyzing the reaction

ATP + deamide-NAD + L-Gln +

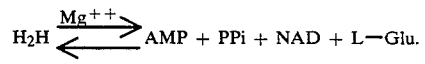

The enzyme uses ammonia or ammonium ion as a substrate, but does not use either glutamine or asparagine. Also disclosed is an assay method using the enzyme, for any one of ATP, deamide-NAD, ammonia or ammonium ion in a specimen to be assayed.

19 Claims, 6 Drawing Sheets

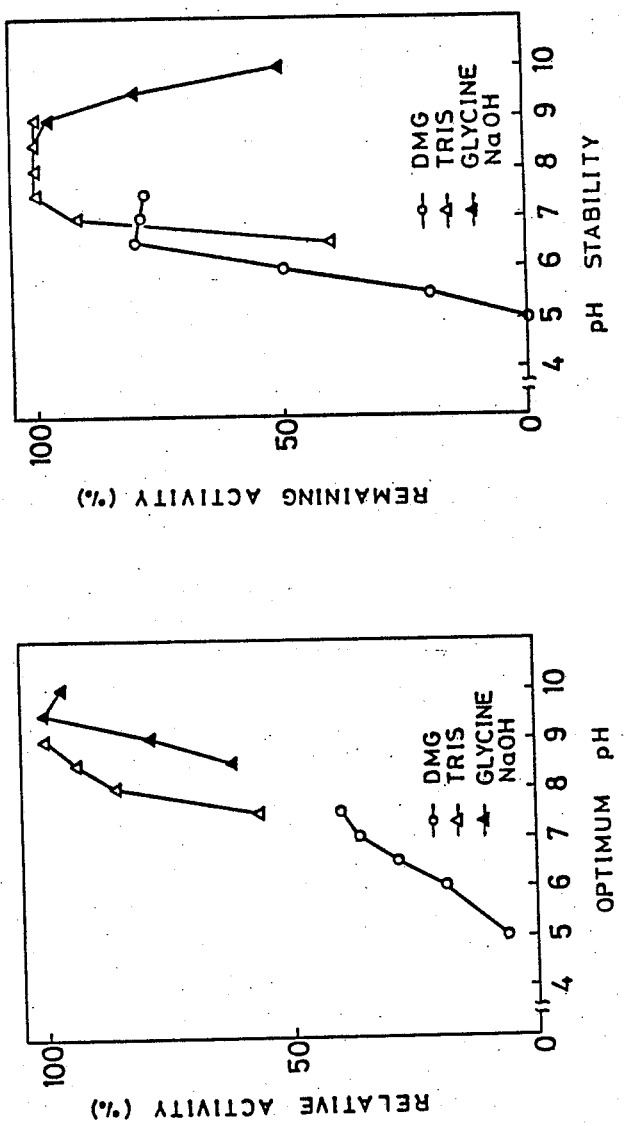

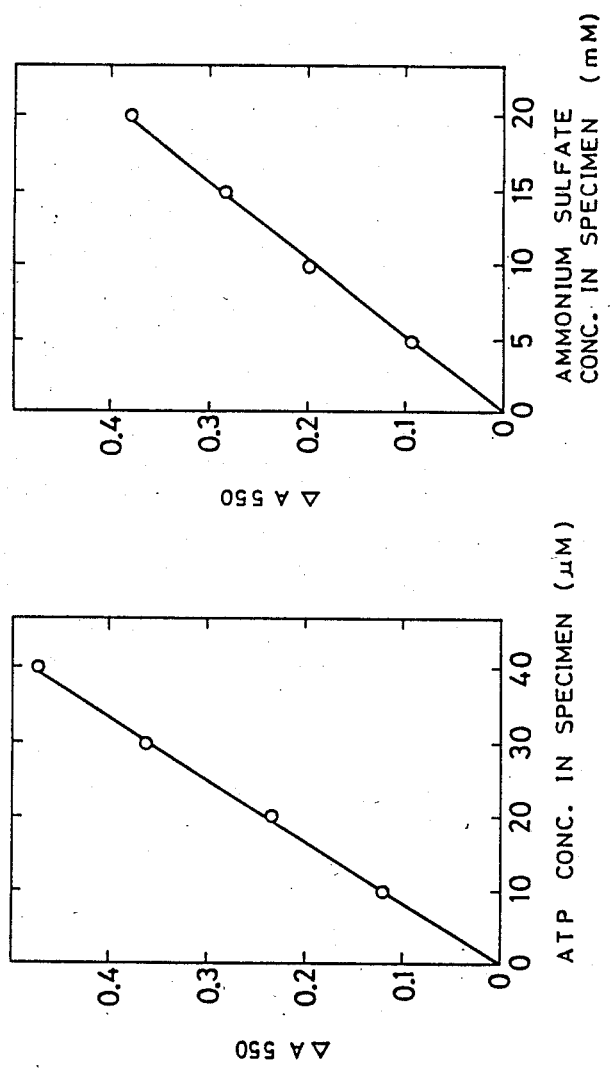

NOVEL NAD SYNTHETASE, ASSAY METHOD USING SAID NOVEL NAD SYNTHETASE AND A PROCESS FOR PRODUCTION THEREOF

BACKGROUND OF THE INVENTION

1. Field of the Invention

The present invention relates to a novel NAD synthetase, a process for production of said enzyme and an assay method using the same.

More particularly, the present invention relates to a novel NAD synthetase, which at least catalyzes the reaction (a) hereinbelow in the presence of $Mg++$ or $Mn++$ ion, and does not catalyze the reaction (b) hereinbelow in the presence of $Mg++$ ion, utilizes ammonia including ammonium ion as a substrate, and does not utilize at least glutamine and asparagine as a substrate, to a process for production of the same, and to an assay method of any one of ATP, deamide-NAD and ammonia including ammonium ion in a specimen by incubating the said specimen with the present NAD synthetase.

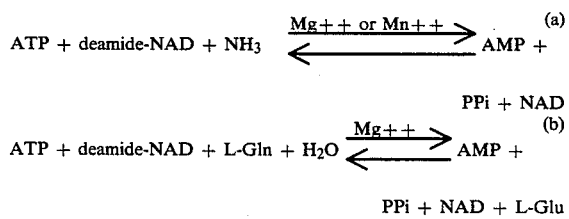

2. Description of the Prior Art

Heretofore, NAD synthetase has been known to exist in rat liver [J. Biol. Chem. 233, 493–500 (1958)], porcine liver [ibid., 236, 525–530 (1961)], yeast [ibid., 247, 4794–4802 (1972)] and E. Coli [ibid., 236, 1494–1497 (1961) and 242, 385–392 (1967)].

These NAD synthetases are classified as NAD synthetase (EC 6.3.1.5) which catalyzes the reaction:

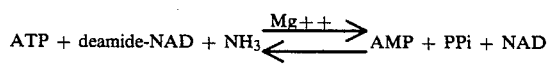

and NAD synthetase (EC 6.3.5.1.) which catalyzes the reaction:

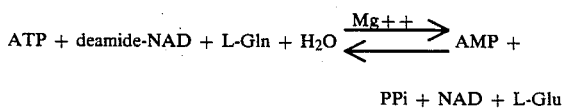

These NAD synthetases utilize $NH_3$ and an amide of L-Gln as a substrate, and are differentiatd by the inhibitory action of azaserine.

Km-values of NAD synthetase (EC 6.3.1.5) are reported as $6.5 \times 10^{-5}$ M ($NH_4+$) and $1.6 \times 10^{-2}$ M (L-Gln) [J. Biol. Chem., 1494–1497, (1961), ibid., 242, 385–392 (1967)] and Km-values of NAD synthetase (EC 6.3.5.1) are reported as $6.4 \times 10^{-8}$ M ($NH_4+$) and $5 \times 10^{-8}$ M (L-Gln) [J. Biol. Chem., 247, 4794–4802 (1972), ibid. 233, 493–500 (1958)].

An assay method for NAD synthetase has been reported, in which the generated NAD is reduced by alcohol dehydrogenase (EC 1.1.1) and the absorbency of the generated reduced NAD (hereinafter designated NADH) is spectrophotometrically measured at 340 nm, or the generated NAD is measured by fluorometry.

The above method assays a component in a specimen, selected from ATP, deamide-NAD and an amide donor, and comprises, as a main reaction step, incubating the specimen containing ATP, deamide-NAD or an amide donor such as $NH_3$, L-glutamine or L-asparagine, with known NAD synthetase (EC 6.3.1.5 and EC 6.3.5.1) in the presence of ATP, deamide-NAD, an amide donor and $Mg++$ to generate NAD, and further comprises, as a side reaction, performing coenzyme cycling reaction by combining the oxidation-reduction reaction system of coenzyme NAD with the oxidation-reduction reaction system of coenzyme reduced NAD, whereafter a consumed or generated component in the said cycling reaction is measured to effect the assay (Japan Unexam. Pat. Publ. No. 59-198995).

As explained, known NAD synthetases utilize an amide donor substrate of L-glutamine, whereas the present NAD synthetase, which catalyzes at least the reaction (a) hereinbelow in the presence of $Mg++$ or $Mn++$ ion, and does not catalyze the reaction (b) hereinbelow in the presence of $Mg++$ ion, utilizes ammonia including ammonium ion as a substrate and does not utilize at least glutamine and asparagine as a substrate, is heretofore unknown.

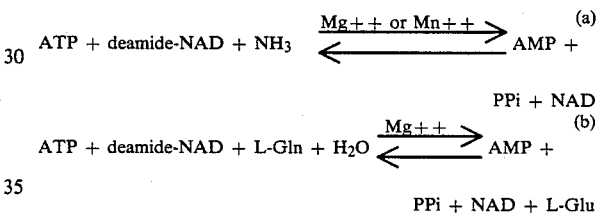

Also, the known NAD synthetases have substrate specificity on L-glutamine, and so $NH_3$ cannot be measured using these enzymes in the presence of L-glutamine.

SUMMARY OF THE INVENTION

We have found that a strain of Bacillus, namely sp. H-804, isolated from a soil sample obtained from hot spring water at Tanoyu-machi, Beppu-shi, Oita-ken, Japan, produces the present NAD synthetase, which catalyzes at least the said reaction (a) hereinbelow in the presence of $Mg++$ or $Mn++$ ion, and does not catlayze the said reaction (b) hereinbelow in the presence of $Mg++$ ion, utilizes ammonia including ammonium ion as a substrate, and does not utilize at least glutamine and asparagine as a substrate.

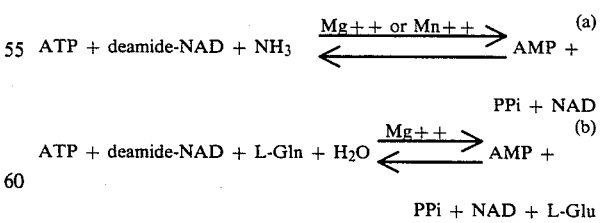

OBJECTS OF THE INVENTION

A first object of the present invention is to provide the present NAD synthetase.

Another object of the present invention is to provide a process for production of the said enzyme.

A further object of the present invention is to provide an assay method for any one of ATP, deamide-NAD and ammonia including ammonium ion in a specimen by incubating the said specimen with the present NAD synthetase, and measuring a component consumed or generated in the ensuring reaction.

BRIEF DESCRIPTION OF THE DRAWINGS

FIG. 1: optimum pH curve of the present NAD synthetase;

FIG. 2: pH-stability curve of the present NAD synthetase;

FIG. 5: assay curve of ATP;

FIG. 6: assay curve of ammonium;

DETAILED DESCRIPTION OF THE INVENTION

Figure 4:
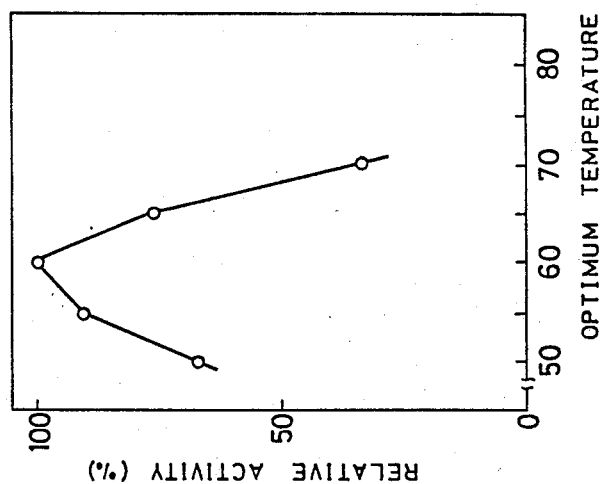
FIG. 4: optimum temperature curve of the present NAD synthetase.

Taxonomical properties of the strain which produces the present NAD synthetase are as follows:

A. Morphological properties:

Observed by microscope on nutrient agar slant medium at 50° C. for 1-3 days cultivation.

1. Form and arrangement: round edges, straight or slightly curved bacilli, single or binary chains.
2. Size: 0.5–1.0×1.6–5.5 μm.
3. Motility: motile by peritrichous flagella.
4. Spores: forms center or subterminal, 0.8–1.0×1.0–1.5 μm, swelling the sporangia.

B. Growth on various media (at 50° C.):

1. Nutrient agar plate: colonies grayish to pale yellowish white with semi-transparent, weak linear growth. No soluble pigment formation.
2. Nutrient agar slant: grayish to pale yellowish with semi-transparent, round plain colonies. No soluble pigment formation.
3. Bouillon agar: uniformly turbid, good growth. Precipitate forms in 2-3 days.
4. BCP milk: no change.

C. Physiological properties (+: positive, −: negative):

| | |
|---|---|
| Gram's stain | + |
| KOH reaction | − |
| acid-fast staining | − |
| capsulation | − |
| anaerobic growth | − |
| catalase production | + (weak) |
| oxidase production | + (weak) |
| urease formation | |
| (SSR medium) | − |
| (Chris. medium) | − |
| lecithinase production | no growth |
| gelatin hydrolysis | + |
| starch hydrolysis | + |
| casein hydrolysis | + |
| esculin hydrolysis | + |
| arginine hydrolysis | − |
| cellulose hydrolysis | − |
| indole production | − |
| $H_2O$ production | + (lead acetate paper) |
| acetonin production | − |
| MR test | − |
| nitrate reduction | − |
| growth on NaCl added medium | + |
| growth on 0.1% NaCl added medium | + |
| growth on 0.25% NaCl added medium | + |
| growth at 65° C. | + |
| growth at 50° C. | + |
| growth at 37° C. | − |
| growth at pH 9.0 | − |
| growth at pH 8.0 | + |
| growth at pH 5.6 | + |
| growth at pH 4.8 | − | acid formation from sugar* (no gas formation):

| | | | |
|---|---|---|---|
| adonitol | − | D-mannose | + |
| L(+)arabinose | + | melezitose | + |
| cellobiose | + | melibiose | + |
| dulcitol | − | raffinose | + |
| meso-erylthritol | − | rhamnose | − |
| D-fructose | − | D-ribose | + |
| fucose | − | salicine | − |
| D-galactose | + | L-sorbose | − |
| D-glucose | + | sorbitol | − |
| glycerin | + | starch | + |
| inositol | − | saccharose | + |
| inilin | − | trehalose | + |
| lactose | + | D-xylose | |
| maltose | − | | |
| D-mannitol | + | | |

OF test (Hugh-Leifson medium) . NT (no change)
OF test (modified)** O (oxidation)

*basal medium: (sugar added ammonium medium)(ASS)

| | | | |
|---|---|---|---|
| (NH4)2HPO4 | 1.0 g | KCl | 0.2 g |
| MgSO4.7H2O | 0.2 g | Yeast ex | 1.0 g |
| Agarose | 3.0 g | BTB | 0.02 g |
| Distilled water | 1000 ml | pH | 7.0 |

**modified medium: 10.0 g glucose added to basal medium.

Utilization test:

| | Simmons medium | Christensen medium |
|---|---|---|
| citrate | − | − |
| malonate | − | − |
| gluconate | − | + |
| propionate | − | − |
| maleinate | − | − |
| succinate | − | + |
| malate | + | + |

According to the above taxonomical properties, present strain H-804 is a bacterium having the characteristics of round edges, straight or slightly curved bacilli, Gram-positive, sporulating at 0.5–1.0×1.6–5.5 μm thermophilic bacterium, weak catalase and oxidase production, no motile and oxidative degradation of sugar (glucose). Comparing these taxonomical properties with *Bergey's Manual*, 8th Ed., 1974, *Manual of Medicinal Bacteriology*, 2nd Ed., 1974 and *Agriculture Handbook*, p. 427, "The genus Bacillus", the present strain is characterized by spore formation and aerobic growth and as so is referred to as genus Bacillus. Among the strains belonging to genus Bacillus that are thermophilic or thermotolerant, (a) *Bacillus subtilis*, (b) *Bacillus coagulance*, (c) *Bacillus liqueniformis*, (d) *Bacillus brevis* and (e) *Bacillus stearothermophilus* can be mentioned. The present strain can be grown at over 30° C., and hence (A) *Bacillus stearothermophilus* and (B) *Bacillus brevis* are suggested. A comparison of these strains with the present strain is as follows: (+: positive, −: negative, d: different in strain)

| Size (μm) | H-804 | (A) | (B) |
| --- | --- | --- | --- |
| width | 0.5–1.0 | 0.5–0.1 | 0.6–0.9 |
| length | 1.6–5.5 | 2–3.5 | 1.5–4.0 |
| Gram's strain | +(decolor) | indefinite | indefinite |
| sporulation | + | + | + |
| swelling of spore | + | + | + |
| motility | − | + | + |
| catalase production | (+) | + | + |
| anaerobic growth | − | − | − |
| acetoin production | − | − | − |
| growth temperature | | | |
| max. (°C.) | >65 | 65–75 | 40–60 |
| min. (°C.) | >37 | 30–45 | 10–35 |
| growth at pH 5.7 | + | − | d |
| growth at 5% NaCl added medium | − | d | − |
| acid formation from sugar: | | | |
| glucose | + | + | + |
| arabinose | + | d | − |
| xylose | + | d | − |
| mannitol | + | d | d |
| gas production from sugar | − | − | − |
| starch hydrolysis | + | + | d |
| citrate utilization | − | − | d |
| nitrate reduction | − | d | d |
| indole production | − | − | − |
| caseine hydrolysis | + | d | + |

The properties of the present strain are quite similar to those of *Bacillus stearothermophilus*, it is reported that the non-motile strain can easily be obtained, and a comparison of the other properties suggested the similarity of the present strain with *Bacillus stearothermophilus*. The present strain is thus named *Bacillus sterothermophilus* H-804. The strain has been deposited in the Fermentation Research Institute and assigned FERM BP-1408.

In the present invention, among the present NAD synthetase-producing microorganisms belonging to the genus Bacillus, the above strain is an example, but any strain which belong to the genus Bacillus and produces the present NAD-synthetase can be used.

Also, an artificial mutant can be prepared by isolating DNA bearing the genetic code of the present NAD synthetase, by recombinant DNA technology from the present NAD synthetase-producing microorganisms, cloning the said NAD into other microorganisms which do not produce the present NAD synthetase, and thus imparting to said other microorganisms the ability to produce the present NAD synthetase. The present enzyme produced by such mutants and an assay method using the same are included in the scope of the present invention.

An NAD-synthetase-producing microorganism belonging to the genus Bacillus is cultured in a conventional medium for enzyme production. Cultivation is carried out in liquid or solid culture, and submerged aeration culture is preferred for industrial production.

The nutrient sources of the medium can be conventional media for microorganism cultivation. Examples of carbon sources are assimilable carbon compounds such as glucose, sucrose, lactose, maltose, starch, dextrin, molasses or glycerin. Examples of nitrogen sources are assimilable nitrogen sources such as corn steep liquor, soybean powder, cotton seed powder, wheat gluten, peptone, meat extract, yeast extract or casein hydrolyzate. Salts such as magnesium, potassium, sodium, zinc, iron, manganese, phosphate or halogen, can be used.

The culturing temperature for *Bacillus stearothermophilus* H-804 is chosen with regard to the growth of NAD-synthetase-producing microorganisms and the production of the enzyme, and is 48°–70° C., preferably 55°–60° C. The culturing time can be varied depending on the culturing conditions, and is generally 10–20 hours. Naturally, cultivation should be stopped upon maximum production of enzyme. The aeration agitation speed is usually 200–400 r.p.m.

Since the enzyme is an endo-enzyme, the cultured cells are collected by means of filtration or centrifugation, and the collected cells are mechanically disrupted by ultrasonication. This is followed by French pressing or glass bead treatment, or enzymatic digestion by lysozyme, with the addition, if necessary, of surface active agents such as Triton X-100 (trade name) or Adekatol SO-120 (trade name).

The enzyme solution is, with or without concentration, subjected to slating-out by adding soluble salts such as ammonium sulfate, or treated by adding a water-miscible organic solvent such as methanol, ethanol, acetone or isopropanol to precipitate the enzyme. The precipitation is dissolved in water or a buffer solution, dialyzed if necessary, and chromatographed by an ion exchange resin such as DEAE-Sephadex, DEAE-Sepharose, carboxymethyl cellulose, carboxymethyl Sepharose or carboxymethyl Sephadex, or by gel-filtration using a molecular sieve such as Sephadex G-200, Sephadex CL-6B or Sephacryl S-200 (trade name). If required, stabilizing agents are added and lyophilized to prepare purified enzyme.

The biochemical properties of the above NAD synthetase are as follows:

(1) Molecular weight: approximately 50,000 [gel filtration with polyvinyl-gel (trade name GPC 3,000 SW: Toyo Soda Co.), using column (7.5 mm ID×60 cm). Standard proteins: aldorase (rabbit muscle, M.W. 150,000), bovine serum albumin (M.W. 67,000), avoalbumin (egg: M.W. 45,000) and cytochrome C (horse heart, M.W. 13,000)]

(2) Isoelectric point: approximately pH 4.6 (electrophoresis using carrier-Ampholite, using a column (24×30 cm LKB Co.), 700 V, 48 hrs. cutting each 2 cm, measured pH and activity)

$Mg^{++}$ or $+Mn^{++}$ (3) Activity: ATP+deamide-NAD+$NH_3$→ATP+-PPi+NAD (4) Substrate specificity:

$NH_3$ including ammonium ion.

In an assay method for enzyme activity hereinafter described $(NH_4)_2SO_4$ 25 mM is replaced by L-valine, L-homoserine, L-serine, L-alanine, L-methionine, L-tyrosine, L-threonine, L-leucine, L-isoleucine, L-arginine, L-phenylalanine, L-histidine, L-asparagine and L-glutamine, and the enzymatic activity is measured. Relative activity of the present enzyme on these amino acids is 0.0 when that on $(NH_4)_2SO_4$ is set at 100. Therefore the present enzyme can utilize only ammonia including ammonium ion as a substrate, but does not utilize at least the above-mentioned amino acids.

(5) Optimum pH:

Reaction medium I, identified hereinafter under the assay method for enzymatic activity, is mixed with dimethylglutarate-NaOH buffer (pH 5.0–7.0), Tris-HCl buffer (pH 6.5–9.0) and glycine-NaOH buffer (pH 8.5–10.0), and the enzymatic activity is measured after stopping the enzyme action by heating at 100° C. for 10 minutes. As shown in FIG. 1, the optimum pH is pH 8.5–10.0.

(6) pH stability:

The present enzyme is dissolved in 50 mM dimethylglutarate-NaOH buffer (pH 5.0-7.0), Tris-HCl buffer (pH 6.5-9.0), or glycine-NaOH buffer (pH 8.5-10.0), and the solution is incubated at 60° C. for 15 minutes. The remaining enzymatic activity is measured by means of an assay method for enzyme activity. The results are shown in FIG. 2, wherein the enzyme is stable at pH 7.5-9.0.

Figure 3:
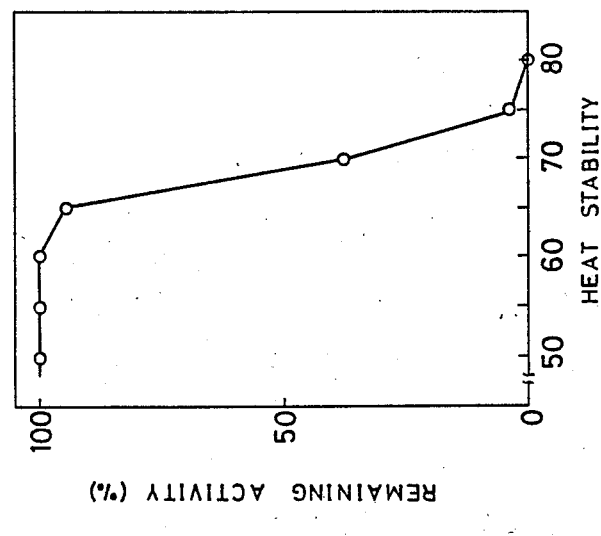
FIG. 3: heat-stability curve of the present NAD synthetase.

(7) Heat stability:

The present enzyme dissolved in 50 mM Tris-HCl buffer (pH 8.0) is held at various temperatures for 15 minutes each, and the remaining enzymatic activity is measured. The results are shown in FIG. 3, wherein the enzyme is stable at least below 60° C.

(8) Optimum temperature:

The present enzyme is mixed with the reaction medium I hereinafter identified under the assay method for enzymatic activity, and incubated at temperatures of 50° C., 55° C., 60° C., 65° C. and 70° C. for 10 minutes each, immediately whereafter the mixture is cooled, and reaction medium II (defined hereinafter under the assay method for enzymatic activity) is added thereto at 37° C., then the enzymatic activity is measured. Results are shown in FIG. 4, wherein the optimum temperature is approximately 60° C.

(9) Effect of enzyme activators and inhibitors:

In an assay for enzymatic activity, each metal ion (5 mM), EDTA (20 mM) or each surface active agent (0.1%) in Table 1 is added separately to the reaction medium I, and the enzymatic activity is measured. Results are shown in Table 1. The enzyme is inhibited by Ni ion ($NiCl_2$, 5 mM) and no activity is observed in EDTA (20 mM).

Furthermore, $MgCl_2$ (5 mM) is replaced by $MnCl_2$ (3 mM) in the reagent identified in the enzymatic assay method hereinafter. Enzyme activity is increased 150% in the presence of $MnCl_2$ (3 mM) as compared with $MgCl_2$ (5 mM).

TABLE 1

| | Concentration | Relative activity | |
|---|---|---|---|
| No addition* | — | 100 | (%) |
| LiCl | 5 mM | 100 | |
| $KNO_3$ | " | 99.2 | |
| KCN | " | 100 | |
| NaCl | " | 102.4 | |
| $NaNO_3$ | " | 96.8 | |
| $NaN_3$ | " | 102.4 | |
| $CaCl_2$ | " | 48.4 | |
| $BaCl_2$ | " | 89.5 | |
| $MnCl_2$ | " | 54.0 | |
| $NiCl_2$ | " | 7.3 | |
| CsCl | " | 100 | |
| $AlCl_3$ | " | 73.4 | |
| $FeCl_3$ | " | 88.4 | |
| EDTA | 20 mM | 0 | |
| Triton X-100 | 0.1% | 109.6 | |
| Nonidet P-40 | " | 103.9 | |
| Adekatol PC-8 | " | 98.7 | |
| Adekatol SO-120 | " | 99.1 | |
| Deoxycholate | " | 104.7 | |
| Brig 35 | " | 102.2 | |

*$MgCl_2$ (5 mM) is added. The other reactons similarly contain $Mg^{++}$ in addition to each specified additive.

(10) Assay method for enzymatic activity:
Reaction medium I:
  50 mM Tris-HCl buffer pH 8.0
  1 mM KCl
  5 mM $MgCl_2$
  0.05% bovine serum albumin
  2 mM ATP
  0.5 mM deamide-NAD
  25 mM $(NH_4)_2SO_4$
Reaction medium II:
  50 mM Tris-HCl buffer pH 8.0
  10 U diaphorase (Toyo Jozo Co. from genus Bacillus)
  3% ethanol
  10 U alcohol dehydrogenase/ml (Toyo Jozo, yeast)
  0.025% NTB (nitrotetrazolium blue)
  0.1% Triton X-100
  10 mM EDTA Reaction medium I (0.3 ml) in a test tube is preincubated at 37° C., and the enzyme solution (5 μl) is added thereto, whereafter the mixture is incubated at 37° C. for exactly 10 minutes.

Reaction medium II (0.8 ml) is added thereto to stop the reaction and simultaneously to start the cycling reaction at 37° C. for exactly 5 minutes. After stopping the cycling reaction by adding 0.1 N-HCl (2.0 ml), the absorbency at 550 nm is measured to calculate the enzyme activity. The enzyme activity is calculated by the following equation:

NAD synthetase activity (mU/ml) =

$$\frac{\Delta A_{550}}{\Delta S_{550}} \times \frac{1.0}{0.005} \times \frac{f}{10}$$

wherein
ΔA: absorbency of specimen,
ΔS: absorbency of standard solution (0.1 mM NAD),
0.005: specimen volume (ml),
10: reaction time,
f: dilution ratio.

The reaction system of the present invention is summarized as follows:

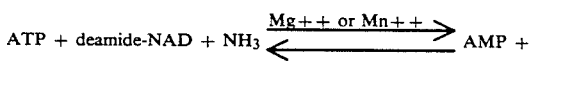

$$ATP + \text{deamide-NAD} + NH_3 \underset{}{\overset{Mg^{++} \text{ or } Mn^{++}}{\rightleftharpoons}} AMP +$$

PPi + NAD

A specimen for an assay according to the present invention can be a specimen containing at least ATP, deamide-NAD or ammonia including ammonium ion, for example a specimen previously containing any one of these components or a specimen in which one of these components is consumed or generated.

A preferred example of the above enzyme reaction system is a reaction system which consumes or generates ATP, deamide-NAD or $NH_3$ including ammonium ion, without the coenzyme NAD and NADH, as in the following non-limiting examples.

1. Enzymatic reaction systems which generate ATP:
  (1) creatine kinase (EC 2.7.3.2): reducing agent

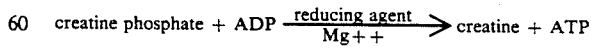

creatine phosphate + ADP $\xrightarrow[Mg^{++}]{\text{reducing agent}}$ creatine + ATP reducing agent: β-mercapto ethanol, reduced glutathione, cysteine, N-acetylcysteine, dithiothreitol, etc.

(2) pyruvate kinase (EC 2.7.1.40):

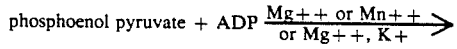

phosphoenol pyruvate + ADP $\xrightarrow[\text{or } Mg^{++}, K^+]{Mg^{++} \text{ or } Mn^{++}}$ -continued (3) acetate kinase (EC 2.7.2.1):

$$\text{acetylphosphate} + \text{ADP} \xrightarrow{Mg^{++} \text{ or } Mn^{++}} \text{acetate} + \text{ATP}$$

(4) carbamate kinase (EC 2.7.2.2):

$$\text{carbamoylphosphate} + \text{ADP} \xrightarrow{Mg^{++}} NH_3 + CO_2 + \text{ATP}$$

(5) aspartate kinase (EC 2.7.2.4):

$$\text{4-phospho-L-aspartate} + \text{ADP} \xrightarrow{Mg^{++}} \text{L-aspartate} + \text{ATP}$$

(6) phosphoglycerate kinase (EC 2.7.2.3.):

$$\text{1,3-diphospho-D-glycerate} + \text{ADP} \xrightarrow{Mg^{++} \text{ or } Mn^{++}}$$
$$\text{3-phospho-D-glycerate} + \text{ATP}$$

(7) arginine kinase (EC 2.7.3.3):

$$\text{arginine phosphate} + \text{ADP} \xrightarrow{Mg^{++} \text{ or } Mn^{++}}$$
$$\text{L-arginine} + \text{ATP}$$

2. Enzymatic reaction systems which utilize ammonium generating soluble ammonium salts or $NH_3$:
  (1) Examples of water-soluble ammonium salts are inorganic or organic ammonium salts which generate ammonium ions, such as ammonium chloride, aqueous ammonia, ammonium sulfate, ammonium nitrate, ammonium acetate, ammonium citrate, etc.
  (2) nicotine amidase (EC 3.5.1.19):

nicotine amide + $H_2O \rightarrow$ nicotinate + $NH_3 + H^+$ (3) glutamyl-peptide-glutaminase (EC 3.5.1.44):

L-glutaminyl-peptide + $H_2O \rightarrow$ L-glutamyl-peptide + $NH_3$ (4) arginine deaminase (EC 3.5.3.6):

L-arginine + $H_2O \rightarrow$ citrulline + $NH_3 + H^+$ (5) guanine deaminase (EC 3.5.4.3):

guanine + $H_2O \rightarrow$ xanthine + $NH_3 + H^+$ (6) adenosine deaminase (EC 3.5.4.4):

adenosine + $H_2O \rightarrow$ inosine + $NH_3 + H^+$ (7) creatinine deaminase (EC 3.5.4.21):

creatinine + $H_2O \rightarrow$ N-methylhydantoin + $NH_3 + H^+$ (8) threonine dehydratase (EC 4.2.1.16):

L-threonine + $H_2O \rightarrow$ 2-oxobutyrate + $CO_2 + NH_3 + H^+$ (9) aspartate ammonium-lyase (EC 4.3.1.1):

L-aspartate $\rightarrow$ fumarate + $NH_3 + H^+$

(10) L-methionine-$\gamma$-lyase (EC 4.4.41.11):

L-methionine + $H_2O \rightarrow$ 2-oxobutyrate + methanethiol + $NH_3 + H^+$

(11) methylaminoglutamatemethyl transferase (EC 2.1.1.21):
  N-methylglutamate + $NH_3 + H^+ \rightleftarrows$ glutamate + methylamine 3. Enzymatic reaction system utilizing AMP for assaying deamide-NAD or $NH_3$ including ammonium ion in a specimen: Adenylate kinase (EC 2.7.4.3):

$$AMP + ATP \rightleftarrows ADP + ADP$$

pyruvate kinase (EC 2.7.1.40):

$$ADP + \text{phosphoenol pyruvate} \rightleftarrows ATP + \text{pyruvate}$$

(1) pyruvate oxidase (EC 1.2.3.3):

$$\text{pyruvate} + Pi + O_2 + H_2O \rightleftarrows \text{acetyl phosphate} + CO_2 + H_2O_2$$

Thus-generated $H_2O_2$ is measured in the presence of peroxidase, and $NH_3$ including ammonium ion or deamide-NAD in a specimen is measured.

(2) lactate dehydrogenase (EC 1.1.1.27):

$$\text{pyruvate} + NADH + H^+ \rightarrow \text{L-lactate} + NAD$$

Decrease of $A_{340}$ according to an oxidation of NADH is measured in the presence of excess lactate dehydrogenase and NADH.

As illustrated hereinabove, in the present invention, not only reaction mixtures containing ATP or $NH_3$ that is consumed or generated in the illustrated enzymatic reaction system, but also reaction mixtures for measuring enzymatic activity that are used in the enzymatic reaction system, consumed substrate or generated product, can be used as a specimen to be assayed.

In these enzymatic reaction systems, ATP or $NH_3$ is assayed for the purpose of determining the enzymatic activity in the said enzymatic reaction or measuring any one of the components thereof. A substance other than the component to be assayed is added at a constant rate as a reagent. The amount of the specimen or reagent can be varied depending on the objects and conditions.

Examples of oxidation-reduction systems with coenzyme NAD are reaction systems constituting dehydrogenase ($E_1$) that consumes NAD to generate NADH and its substrate ($S_1$), or dehydrogenase ($E_1$) with coenzyme NAD or NADP and its substrate ($S_1$). The source of the dehydrogenase is not limited and at least this enzyme reacts with specific substrates and consumes coenzyme NAD to form NADH.

Examples of these enzymes and substrates are mentioned in *Enzyme Handbook*. Examples are as follows:
  lactate dehydrogenase (EC 1.1.1.27) and L-lactate,
  glycerol dehydrogenase (EC 1.1.1.6) and glycerol,
  glycerol-3-phosphate dehydrogenase (EC 1.1.1.8) and glycerol-3-phosphate,
  glucose dehydrogenase (EC1.1.47) and glucose,
  malate dehydrogenase (EC 1.1.1.37) and L-malate,
  glutamate dehydrogenase (EC 1.4.1.2) and L-glutamate, 3-α-hydroxysteroid dehydrogenase (EC 1.1.1.50) and 3-α-hydroxysteroid.

The amount of enzyme used in these oxidation-reduction reactions varies depending on the enzyme activity, the kind of substrate and the ration of coenzyme cycling. The substrate should be in molar excess as compared with the cycling coenzyme, because one mole of substrate is consumed per cycle, and so the amount of substrate is determined by the number of cycles per hour and the reaction time. The concentration of the substrate is preferably selected to attain a maximum reaction rate of oxido-reductase, and is 0.1 mM–100 mM.

The reaction system for coenzyme NADH is a reaction system of functional substances ($E_2$), which at least consumes NADH and generates NAD, and its substrate ($S_2$). Examples thereof are a reaction system with oxidoreductase, which at least consumes NADH and generates NAD, and its substrate, and a reaction system consisting of an electron-transfer agent and a tetrazolium salt.

Coenzyme cycling reaction system:

(a) oxidation-reduction reaction system with coenzyme NAD;

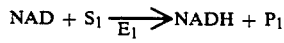

(b) transfer reaction system with coenzyme NADH;

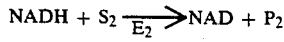

wherein;

$NH_3$: compound containing monovalent ammonium ion, $E_1$: dehydrogenase which catalyzes a reaction consuming the substrates NAD and $S_1$, and generating NADH and $P_1$.

$E_2$: active substance which catalyzes a reaction consuming NADH and $S_2$, and generating NAD and $P_2$, $S_1$: reduced substrate in $E_1$, $S_2$: oxidized substrate in $E_2$, $P_1$: oxidation product of $S_1$, $P_2$: reduction product of $S_2$.

A reaction utilizing $NH_3$ is illustrated as follows:

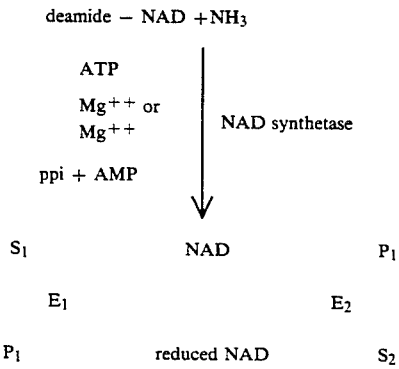

Examples of oxidoreductase hereinabove are a dehydrogenase which catalyzes, with at least coenzyme NADH, a reaction or an excess amount of specific substrate ($S_2$) to form NAD and reduced substrate ($P_2$) of $S_2$; or NADH: (acceptor) oxidoreductase wherein at least NADH is the coenzyme and the acceptor is cytochrome, a disulfide compound, quinone and its analogues, but the origin is not limited. These enzymes, substrates and acceptors are mentioned in *Enzyme Handbook*.

Examples of dehydrogenase and its substrate are lactate dehydrogenase (EC 1.1.1.27) and pyruvate, alcohol dehydrogenase (EC 1.1.1) and acetaldehyde, glycerol dehydrogenase (EC 1.1.1.6) and dihydroxyacetone.

Examples of NADH: (acceptor) oxidoreductase are cytochrome $b_5$ reductase (EC 1.6.2.2) and diaphorase.

Examples of acceptors are methylene blue, flavins, quinones and 2,6-dichlorophenol indophenol.

The combination of NADH: (acceptor) oxidoreductase and acceptor is not limited to an enzyme with coenzyme NADH and an electron acceptor, and is preferably diaphorase (EC 1.6.4.3) and tetrazolium salt, and methylene blue, NAD dehydrogenase (EC 1.6.99.3) and cytochrome c. The concentration thereof is usually 0.05–100 U/ml. The concentration of the tetrazolium salt depends upon solubility of the tetrazolium salt and the ultimately generated formazan, and is generally 1–100 ug per one ml of reagent.

Examples of electron transfer agents are substances which have an activity for oxidizing NADH to NAD without detrimental effect on coenzyme cycling, for example phenazine methosulfate, meldola blue or pyrocyanine. The concentration thereof depends on the cycling ratio and is 5 ug–0.5 mg per ml of reaction mixture.

The above cycling reaction is carried out usually at room temperature to 37° C., preferably at 30°–37° C. The reaction time is not limited but is usually at least one minute, preferably at least 5 minutes. The reaction can be terminated by adding an acid such as hydrochloric acid or phosphoric acid.

After terminating the cycling reaction, the consumed or generated substance in the cycling reaction is measured. Examples thereof are the reduction product ($P_1$) from the reduced substrate ($S_1$) of $E_1$, or the reduced product ($P_2$) from the oxidized substrate ($S_2$) of $E_2$ as a generated component, and the reduced substrate ($S_1$) of $E_1$ or the oxidized substrate ($S_2$) of $E_2$ as a consumed component. One of the components $P_1$, $P_2$, $S_1$ or $S_2$ is measured. Most preferably, the product which is colorless as substrate and is colored or fluorescent as product, is colorimetrically measured by absorbency changes. For example, formazan generated from substrate ($S_2$) tetrazolium is reduced to form a reduced product ($P_2$) which is measured colorimetrically. Furthermore, when flavins or quinones are used as substrate ($S_2$), the consumed amount of the substrate ($S_2$) is preferably measured by colorimetry.

In the above reaction, a surface active agent is preferably added for preventing the precipitation of formazan from tetrazolium salt. Examples of surface active agents are non-ionic surface active agents such as Triton X-100 (iso-octyl phenoxy polyethyoxy ethanol, Rohm & Haas Co., USA) or Adekatol SO-120 (ethoxylate or secondary alcohol, Asahidenka Kogyo Co., Japan). The concentration thereof is 0.01–3% for a reagent. Adding a surface active agent provides an increased sensitivity of measurement and stability of formazan pigment.

The colorimetric assay of the generated formazan pigment can be performed by measuring the optical density (OD) at its specific adsorption wavelength such as at 500–550 nm.

In the method of the present invention, an assay method such as an end-point method, a rate assay method or a dry-chemical method (film method, immobilized solid) can advantageously be used.

The method of the present invention is useful for assaying any one of ATP, deamide-NAD, ammonia or ammonium ion, and especially ammonia including ammonium ion can be assayed without affecting amino acid in a specimen. Furthermore, the NAD synthetase enzyme of the present invention is a heat stable enzyme and is preferred for use in an assay method according to the present invention.

The following examples illustrate the present invention but are not to be construed as limiting:

EXAMPLE 1

A liquid medium (pH 7.6, 40 lit.) consisting of peptone 1%, glucose 0.5%, NaCl 0.05% and $MgSO_4 \cdot 7H_2O$ 0.05% a 50 l. jar fermenter was sterilized at 120° C. for 20 mins. A previously cultured *Bacillus stearothermophilus* H-804 seed-culture medium of the same composition (200 ml) was inoculated therein an the mixture was cultured at 60° C. for 10 hours with aeration of 40 l/min. and agitation of 150 r.p.m. After cultivation, the cells were collected by centrifugation, and were suspended in 10 mM Tris-HCl (pH 8.0 500 ml) containing 0.1% lysozyme, and the medium was incubatd at 37° C. for 30 mins. to lyse the cells. The lysed solution was centrifuged at 5,000 r.p.m. for 10 mins. to obtain a supernatant solution (450 ml). Ammonium sulfate was added thereto to fractionate the solution (0.5–0.71 saturation) and the resultant precipitate, dissolved in 10 mM Tris-HCl buffer (50 ml, 21 U), was dialyzed against the same buffer (5 lit.) The precipitated insolubles were removed by centrifugation (15,000 r.p.m., 10 mins.) The supernatant solution (20 U) was charged on a column (2.5×5 cm) of DEAE-Sepharose CL-6B buffered with 10 mM Tris-HCl buffer (pH 8.0) and eluted with gradient of 0–0.5 M NaCl. The fractions eluting with 0.25–0.3 M NaCl were collected (80 ml, 16.5 U), concentrated by ultra-filtration using a CF-25 membrane (Amicon Co. centriflow membrane cone), chromatographed with Sephadex G-100 (3.6×80 cm) and the active fractions collected to obtain the purified solution (5 ml, 14 U).

EXAMPLE 2

Assay of ATP in a specimen:
Reaction medium III:
50 mM Tris-HCl buffer pH 8.0
20 mM KCl
5 mM $MgCl_2$
0.05% bovine serum albumin
1 mM deamide-NAD
50 mM $(NH_4)_2SO_4$
100 mU/ml the present NAD synthetase
Reaction medium IV:
50 mM Tris-HCl buffer pH 8.0
10 U dia-phorase/ml (Toyo Jozo, Bacillus)
3% ethanol
10 U alcohol dehydrogenase/ml (Toyobo, yeast)
0.025% NTB
0.1% Triton X-100
15 mM EDTA Reaction medium III (0.3 ml) in test tubes was pre-incubated at 37° C., and 0, 10, 20, 30 and 40 μM ATP solutions (5 μl each) were added thereto, respectively; then each was incubated at 37° C. for 10 minutes. Reaction medium IV (0.7 ml) was added thereto, and each was incubated at 37° C. for exactly 5 minutes, whereupon the reaction was stopped by adding 0.1 N HCl (2.0 ml) and the absorbency was measured at 550 nm. The results are shown in FIG. 5. As shown in that figure, good linearity was obtained.

EXAMPLE 3

Measurement of ammonium ion:
50 mM $(NH_4)_2SO_4$ in reaction medium III in Example 2 was replaced by 5 mM ATP to prepare the present reaction medium. Various concentrations of ammonium sulfate (0, 5, 10, 15 and 20 μM, 5 μl), were added thereto and treated the same way as in Example 2. As shown in FIG. 6, good linearity was obtained.

EXAMPLE 4

Figure 7:
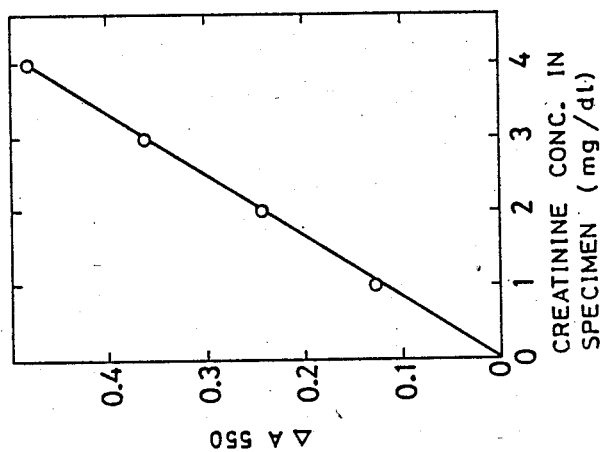
FIG. 7: assay curve of creatinine.

Assay of creatinine:
Reaction medium V:
50 mM Tris-HCl buffer pH 8.0
10 mM KCl
5 mM $MgCl_2$
1 mM ATP
0.05% bovine serum albumin
1 mM deamide-NAD
20 U/ml creatinine deaminase (KODAK)
100 mU/ml the present NAD synthetase Reaction medium V (0.3 ml) in teest tubes was preincubated at 37° C., and 1, 2, 3 and 4 mg/dl creatinine solutions (10 μl each) were added thereto, respectively; whereafter the resulting series of mixtures were treated the same way as in Example 2. As shown in FIG. 7, good linearity was obtained.

EXAMPLE 5

Figure 8:
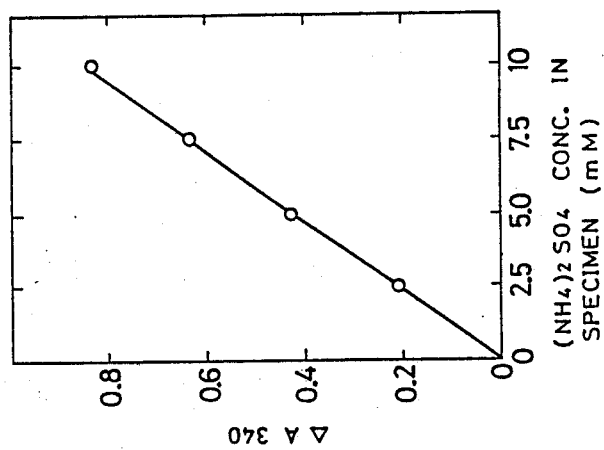
FIG. 8: assay curve of ammonia measured at 340 nm.

Assay of ammonium ion:
Reaction medium VI:
50 mM Tris-HCl buffer pH 8.0
10 mM KCl
5 mM $MgCl_2$
1 mM ATP
0.05% bovine serum albumin
1 mM deamide-NAD
100 mU/ml the present NAD synthetase Reaction medium VI (0.1 ml) in test tubes was preincubated at 37° C., and 0, 2.5, 5.0, 7.5 and 10.0 μM $(NH_4)_2SO_4$ solutions (10 μl each) were added thereto, respectively; then each resulting mixture was incubated at 37° C. for 20 minutes and the absorbency was measured at 340 nm. The results are shown in FIG. 8. As shown in that figure, good linearity was obtained.

EXAMPLE 6

Assay of generated ATP:
Reaction medium VII:
50 mM Tris-HCl buffer pH 8.0
10 mM KCl
5 mM $MgCl_2$
1 mM ATP
0.05% bovine serum albumin
0.05% Triton X-100
1 mM deamide-NAD
10 U/ml myokinase kinase (Sigma, Bacillus)
10 U/ml pyruvate kinase (Sigma, Bacillus)
10 mM phosphoenol pyruvate
100 mU/ml the present NAD synthetase
Reaction medium VIII:
50 mM phosphate buffer pH 8.0

Figure 9:
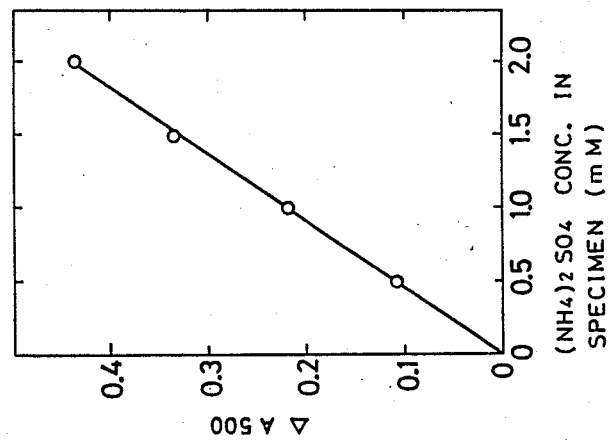
FIG. 9: assay curve of ammonia measured with generated ATP.

100 mU/ml pyruvate oxidase (Sigma, Pediococcus)
100 mU/ml peroxidase (Sigma)
0.2% phenol
0.3% 4-aminoantipyrine Reaction medium VII (1 ml) in test tubes was preincubated at 37° C., and 0, 0.5, 1.5 and 2.0 mM (NH$_4$)$_2$SO$_4$ solutions (10 μl each) were added thereto, respectively; then each resulting mixture was incubated at 37° C. for 30 minutes. Reaction medium VIII (0.1 ml) was added thereto, and each resulting mixture was incubated at 37° C. for 30 minutes and the absorbency was measured at 550 nm. The results are shown in FIG. 9. As shown in that figure, good linearity was obtained.

EXAMPLE 7

Assay of deamide-NAD:
Reaction medium IX:
50 mM Tris-HCl buffer pH 8.0
10 mM KCl
5 mM MgCl$_2$
0.05% bovine serum albumin
50 mM (NH$_4$)$_2$SO$_4$
1 mM ATP
100 mU/ml the present NAD synthetase
3% ethanol
10 U alcohol dehydrogenase
0.1% Triton X-100

Figure 10:
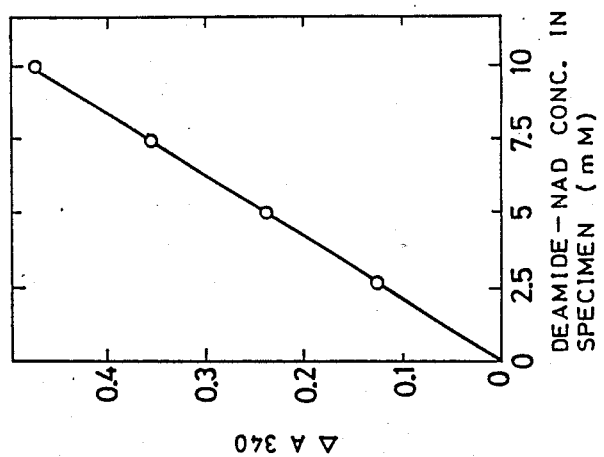
FIG. 10: assay curve of deamide-NAD.

Reaction medium IX (1 ml) in test tubes was preincubated at 37° C., and 0, 2.5, 5 and 10 mM deamide-NAD solutions (10 μl each) were added thereto, respectively; then each resulting mixture was incubated at 37° C. for 30 minutes and the absorbency was measured at 340 nm. The results are shown in FIG. 10. As shown in that figure, good linearity was obtained.

EXAMPLE 8

Optimum concentration of metal ion:
Reaction medium X:
50 mM Tris-HCl buffer pH 8.0
10 mM KCl
2 mM ATP
0.05% bovine serum albumin
0.5 mM deamide-NAD
25 mM (NH$_4$)$_2$SO$_4$
Reaction medium XI:
50 mM Tris-HCl buffr pH 8.0
10 U diaphorase/ml (Toyo Jozo Co., Bacillus)
3% ethanol
10 U alcohol dehydrogenase/ml (Toyobo Co., yeast)
0.025% NTB
0.1% Triton X-100
10 mM EDTA To reaction medium X in test tubes were added 0.25, 0.50, 0.75, 1, 2, 3 and 4 mM MgCl$_2$ and 0.25, 0.50, 0.75, 1, 2, 3 and 4 mM MnCl$_2$, respectively; then each resulting mixture was treated, after adding the present NAD synthetase solution, according to the previously described enzymatic assay method.

Figure 12:
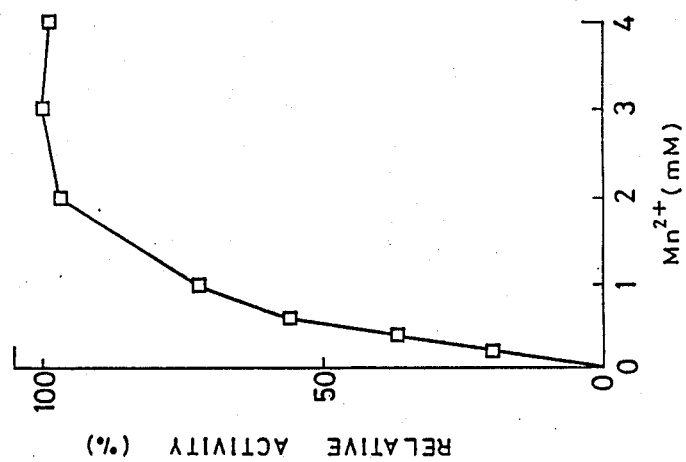
FIG. 12: optimum concentration curve of $MnCl_2$.
Figure 11:
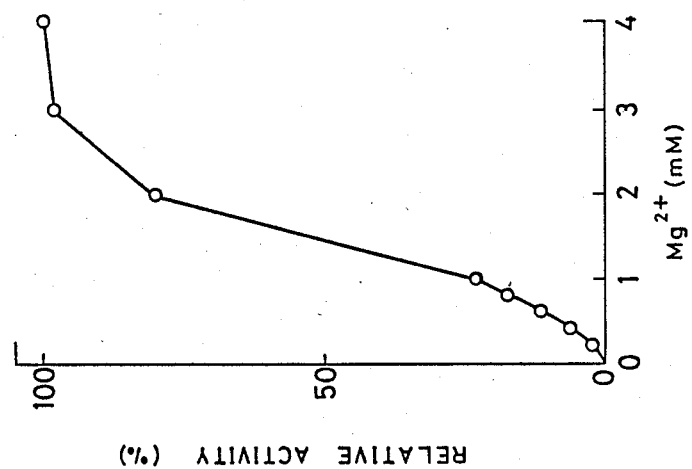
FIG. 11: optimum concentration curve of $MgCl_2$.

The results are shown in FIG. 11 (MgCl$_2$ added group) and FIG. 12 (MnCl$_2$ added group). As shown in that figure, optimum concentration of MnCl$_2$ is at 3 mM.

What is claimed is:

1. NAD synthetase that selectively catalyzes in the presence of Mg++ or Mn++ ion the following reaction:

ATP + deamide-NAD +

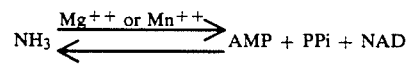

NH$_3$ ⇌ AMP + PPi + NAD without catalyzing in the presence of Mg++ ion the following reaction:

ATP + deamide-NAD + L-Gln +

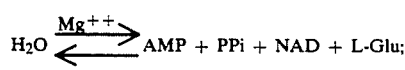

H$_2$O ⇌ AMP + PPi + NAD + L-Glu;

and utilizes ammonia including ammonium ion as a substrate without utilizing glutamine or asparagine as a substrate.

2. NAD synthetase according to claim 1, having an optimum pH of 8.5–10.0, pH-stability in the range of pH 7.5–9.0 (at 60° C., 15 mins.), an optimum temperature of about 60° C., and is stable to heat below 60° C. (at pH 8.0, 15 mins.)

3. NAD synthetase according to claim 2, having an isoelectric point at about pH 5.3, and a molecular weight of 50,000±5,000.

4. Method for assaying a component in a specimen, said component being selected from ATP, deamide-NAD, ammonia and ammonium ion; said method comprising:

incubating a specimen containing at least one of ATP, deamide-NAD, ammonia and ammonium ion with NAD synthetase that selectively catalyzes in the presence of Mg++ or Mn++ ion the following reaction:

ATP + deamide-NAD +

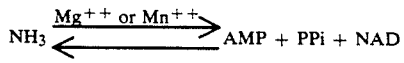

NH$_3$ ⇌ AMP + PPi + NAD without catalyzing in the presence of Mg++ ion the following reaction:

ATP + deamide-NAD + L-Gln +

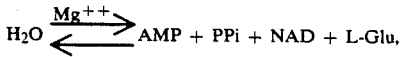

H$_2$O ⇌ AMP + PPi + NAD + L-Glu, utilizes ammonia including ammonium ion as a substrate without utilizing glutamine or asparagine as a substrate, in the presence of ATP, deamide-NAD, ammonia or ammonium ion, and Mg++ ion or Mn++ ion to generate NAD;

subjecting said generated NAD to a coenzyme cycling reaction comprising reducing said generated NAD to reduced NAD, and oxidizing thus-generated reduced NAD to NAD; and measuring a compound consumed or generated in said cycling reaction.

5. Method according to claim 4, wherein said ATP is generated by an enzymatic reaction selected from the group consisting of:
creatine kinase:

creatine phosphate + ADP $\xrightarrow[\text{Mg++}]{\text{reducing agent}}$ creatine + ATP reducing agent: β-mercapto ethanol, reduced glutathione, cysteine, N-acetylcysteine or dithiothreitol; pyruvate kinase:

phosphoenol pyruvate + ADP $\xrightarrow[\text{Mg++, K+}]{\text{Mn++ or Mg++, or}}$ pyruvate + ATP;

acetate kinase:

acetylphosphate + ADP $\xrightarrow{\text{Mg++ or Mn++}}$ acetate + ATP;

carbamate kinase:

carbamoylphosphate + ADP $\xrightarrow{\text{Mg++}}$ NH$_3$ + CO$_2$ + ATP;

aspartate kinase:

4-phospho-L-aspartate + ADP $\xrightarrow{\text{Mg++}}$ L-aspartate + ATP;

phosphoglycerate kinase:

1,3-diphospho-D-glycerate + ADP $\xrightarrow{\text{Mg++, or Mn++}}$ 3-phospho-D-glycerate + ATP;

arginine kinase:

arginine phosphate + ADP $\xrightarrow{\text{Mg++ or Mn++}}$ L-arginine + ATP.

6. Method according to claim 4, wherein said ammonium ion is provided by a member selected from the group consisting of ammonium chloride, aqueous ammonia, ammonium sulfate, ammonium nitrate, ammonium acetate and ammonium citrate.

7. Method according to claim 4, wherein said ammonia or ammonium ion is consumed or generated by an enzymatic reaction selected from the group consisting of:

nicotine amidase:

nicotine amide + H$_2$O $\longrightarrow$ nicotinate + NH$_3$ + H$^+$;

glutamyl-peptide-glutaminase:

L-glutaminyl-peptide + H$_2$O $\longrightarrow$ L-glutamyl-peptide + NH$_3$;

arginine deaminase:

L-arginine + H$_2$O $\longrightarrow$ citrulline + NH$_3$ + H$^+$ guanine deaminase:

guanine + H$_2$O $\longrightarrow$ xanthine + NH$_3$ + H$^+$;

adenosine deaminase:

adenosine + H$_2$O $\longrightarrow$ inosine + NH$_3$ + H$^+$;

creatinine deaminase:

creatinine + H$_2$O $\longrightarrow$ N-methylhydantoin + NH$_3$ + H$^+$;

threonine dehydratase:

L-threonine + H$_2$O $\longrightarrow$ 2-oxobutyrate + CO$_2$ + NH$_3$ + H$^+$;

aspartate ammonium-lyase:

L-aspartate $\longrightarrow$ fumarate + NH$_3$ + H$^+$;

L-methionine-γ-lyase:

L-methionine + H$_2$O $\longrightarrow$ 2-oxobutyrate + CH$_3$SH + NH$_3$ + H$^+$; and methylamino-glutamate methyl transferase:

N-methylglutamate + NH$_3$ + H$^+$ $\rightleftarrows$ glutamate + methylamine.

8. Method according to claim 4, wherein said generated NAD is reduced to said reduced NAD in an enzymatic reaction system comprising dehydrogenase that consumes NAD and generates reduced NAD, and a substrate thereof.

9. An assay method according to claim 8, wherein said dehydrogenase and substrate thereof are selected from the group consisting of:
lactate dehydrogenase and L-lactate;
alcohol dehydrogenase and ethanol;
glycerol-3-phosphate dehydrogenase and glycerol-3-phosphate;
glucose dehydrogenase and glucose;
malate dehydrogenase and L-malate;
glutamate dehydrogenase and L-glutamate; and
3-α-hydroxysteroid dehydrogenase and 3-α-hydroxysteroid.

10. An assay method according to claim 4, wherein said reduced NAD is oxidized to NAD in a reaction system comprising oxido-reductase that consumes reduced NAD and generates oxidized NAD, and a substrate thereof.

11. Method according to claim 10, wherein said oxido-reductase and substrate thereof are selected from the group consisting of:
lactate dehydrogenase and pyruvate;
alcohol dehydrogenase and acetaldehyde;
glycerol dehydrogenase and dihydroxyacetone;
glycerol-3-phosphate dehydrogenase and dihydroxyacetone phosphate;
malate dehydrogenase and oxaloacetate; and
3-α-hydroxysteroid dehydrogenase and 3-ketosteroid.

12. Method according to claim 10, wherein said oxido-reductase and substrate thereof is reduced NAD: (acceptor) oxidoreductase and an acceptor thereof.

13. Method according to claim 12, wherein said reduced NAD: (acceptor) oxidoreductase and said acceptor thereof are reduced NAD dehydrogenase and a member selected from the group consisting of flavins, quinones, 2,6-dichlorophenol indophenol, ferricyanide salt, tetrazolium salt, cytochrome c and oxygen, respectively.

14. Method according to claim 10, wherein said oxidoreductase and substrate thereof are diaphorase tetrazolium salt and resazurium.

15. Method according to claim 4, wherein said reduced NAD is oxidized to NAD by means of an electron-transfer agent and tetrazolium.

16. Method according to claim 15, wherein said electron-transfer agent is selected from the group consisting of phenazine methosulfate, meldola blue and pyrocyanine.

17. Method according to claim 4, wherein said AMP is measured using an enzymatic reaction system selected from the group consisting of:

adenylate kinase:

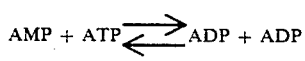

pyruvate kinase:

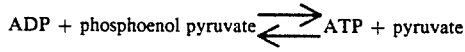

pyruvate oxidase:

pyruvate + Pi + O$_2$ +

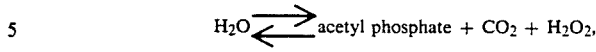

H$_2$O ⇌ acetyl phosphate + CO$_2$ + H$_2$O$_2$, wherein generated H$_2$O$_2$ is measured; and adenylate kinase:

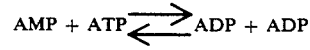

pyruvate kinase:

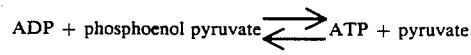

lactate dehydrogenase:

pyruvate + NADH + H$^+$ ⟶ L-lactate + NAD, wherein consumed NADH is measured.

18. Method according to claim 4, wherein said cycling reaction is carried out with added surface active agent.

19. Method according to claim 18, wherein said surface active agent is a non-ionic surface active agent.

* * * * *